United States Patent [19]

Roffey et al.

[11] Patent Number: 4,808,538
[45] Date of Patent: Feb. 28, 1989

[54] METHOD AND DEVICE FOR MEASURING THE CORROSIVITY OF LIQUIDS

[75] Inventors: Roger Roffey; Göran Olofsson; Anders Norqvist, all of Umeå ; Göran Hultén, Bygdeå, all of Sweden

[73] Assignee: Försvarets Forskningsanstalt, Stockholm, Sweden

[21] Appl. No.: 821,554

[22] PCT Filed: Mar. 21, 1985

[86] PCT No.: PCT/SE85/00128

§ 371 Date: Nov. 18, 1985

§ 102(e) Date: Nov. 18, 1985

[87] PCT Pub. No.: WO85/04254

PCT Pub. Date: Sep. 26, 1985

[30] Foreign Application Priority Data

Mar. 21, 1984 [SE] Sweden ............................. 8401581

[51] Int. Cl.[4] .............................................. G01N 17/00
[52] U.S. Cl. ........................................ 436/6; 436/151; 422/53
[58] Field of Search ............... 422/98, 53; 436/6, 151; 73/DIG. 4, 23, 24, 61, 61.1; 310/8.9, 311, 312

[56] References Cited

U.S. PATENT DOCUMENTS

| | | | |
|---|---|---|---|
| 3,164,004 | 1/1965 | King, Jr. ................... | 73/23 |
| 3,253,219 | 5/1966 | Littler ..................... | 73/86 X |
| 3,260,104 | 7/1966 | King, Jr. ................... | 73/23 |
| 3,653,253 | 4/1972 | Olin ........................ | 73/28 |
| 3,677,066 | 7/1972 | King, Jr. et al. ............ | 73/23 |
| 3,863,495 | 2/1975 | Schulz et al. ............... | 73/61.1 C |
| 4,227,398 | 10/1980 | Keirns et al. ............... | 73/61 R |
| 4,539,846 | 9/1985 | Grossman .................... | 422/53 X |

FOREIGN PATENT DOCUMENTS 3021793 12/1980 Fed. Rep. of Germany .

OTHER PUBLICATIONS

R. Roffey, A. Norqvist, and A. Edlund, Microbial Aspects on Oil Storage, pp. 97–114, Proc. Symp. Oil and Appl. Microbial, Publ. The Swedish Academy of Engineering Science, report 278 (1985).

R. Roffey, A. Norqvist, and A. Edlund, Biodeterioration of Jet Fuel During Long-Term Storage in Rock Caverns, In Proc. 6th Int. Biodeter. Symp., Biodeterioration 6, Publ. CAB Slough, UK (1986).

A. Norqvist, R. Roffey, and A. Edlund, Microbial Studies in Rock Caverns with Jet Fuel, Heavy Fuel Oil and Crude Oil, In Proc. 2nd Int. Conf. on Long-Term Storage Stabilities of Liquid Fuels, San Antonio, Texas, USA (1986) in press.

A. Norqvist and R. Roffey, Alternative Method for Monitoring the Effect of Inhibitors on Sulfate Reduction, J. Gen. Appl. Microbial, 29, 335 (1983).

R. Roffey, G. Olofsson, A. Norqvist, and G. Hulten, Method and Device for Measuring the Corrosivity of Liquids, Int. patent G0IN 29/02 17/00, Publ. no. WO 85/04254, PCT Gazette Sect. 1, 21, 2949 (1985).

Roffey et al., "Methods to Monitor Biodeterioration of Jet Fuel During Long Term Storage in Rock Caverns", 1986.

Primary Examiner—Benoît Castel
Attorney, Agent, or Firm—Fleit, Jacobson, Cohn & Price

[57] ABSTRACT

According to the invention a piezoelectric crystal, e.g. a quartz crystal, coated with a metal or another suitable material is exposed to the action of a corrosive liquid, preferably by being immersed therein. The mass change on the crystal surface, caused by the corrosion, and the resulting change in the natural oscillation frequency of the crystal is determined and constitutes a measure of the corrosivity of the liquid. The natural oscillation frequency of the crystal can in this way also be measured in situ in the liquid, in which way the dynamic course of the corrosion reaction can be followed continuously. According to a special embodiment of the invention the sensitivity during the measurement can be increased, if the crystal is pretreated by being activated with a sulphide solution.

7 Claims, 4 Drawing Sheets

METHOD AND DEVICE FOR MEASURING THE CORROSIVITY OF LIQUIDS

BACKGROUND OF THE INVENTION

The present invention relates to a method for measuring the corrosivity of liquids towards primarily metals and to a device for carrying out the method.

When storing petroleum products there are in some cases formed various sulphur compounds because of, for instance, bacterial influence, which compounds will attack metals. These corrosive compounds will form on the surface of the metal a film of molecules consisting of atoms from the corroding metal but also consisting of sulphur, hydrogen etc. This film increases on the metal and may cause big problems. This is especially relevant for oil products, e.g. crude oils, oils for heating purposes and aviation fuels, that are in contact with water. This has been observed when oil products are stored inside rock chambers on a water bed, and this is a serious problem especially when jet fuel is being stored. In the interface between water and oil there are microorganisms, e.g. sulphate-reducing bacteria, that will form sulphur compounds, such as hydrogen sulphide, elementary sulphur and certain organic sulphur compounds, including among others mercaptans, sulphides and disulphides. Said compounds will move upwards into the oil and make it corrosive. If such corrosive oil is used as motor fuel, the motor among other things may become damaged because certain metal parts will corrode, and if the fuel is aviation fuel the corrosion constitutes a potential danger for the safety in flight.

This is why it is very important to have a possibility of determining the corrosivity in an easy but at the same time reliable way, preferably at field locations. Particularly when storing for instance jet fuel over a long period in a rock chamber, there is a great need to be able to discover at a very early stage if the fuel is becoming corrosive. The method should therefore preferably be so adapted that an analysis can be carried out at the very place, for instance at a rock chamber.

It is here not necessary to exactly know the chemical composition of the corrosive compounds. It is fully adequate to learn about for instance how rapidly the surface film, which is formed on a metal immersed in the petroleum product, will increase.

The method that is used today to measure the corrosivity of a petroleum product is an ocular inspection of a metal strip, preferably made of silver, which has been kept in the product in question. A silver strip, which is corroded by sulphur compounds in the petroleum product, becomes black, and a classification from 0 to 4 is used as a graduation of the blackening extent. Even if the test method that is used today is standardized, IP 227/73, 1976, Institute of Petroleum, Standards for petroleum and its products, Methods for analysis and testing, 35th ed., Applied Science Publishers, a subjective estimation is made of the colouration and thus of the corrosiveness. Besides, the method takes a long time to perform, relatively large sample volumes (250 ml) are required, and the classification with five steps is too coarse. Furthermore, a colouration recognizable for the eye cannot be observed until the film thickness exceeds about 100 Å. Therefore it is desirable to have a more rapid and less subjective test method that is more sensitive and more reproducible than the methods used up to now.

SUMMARY OF THE INVENTION

The method of the invention is a simple, reliable and objective measuring method that is easily converted to automatic working. It is more sensitive than the standard method used to now, and films as thin as 1 Å can be detected. The characteristics of the invention are evident from the attached patent claims.

A piezoelectric crystal has a constant natural oscillation ($\nu$) at rest and oscillates at a frequency that is dependent on for instance the mass on its surface. If the crystal is given a coating that interacts or reacts with a component in its environment, the mass on the crystal surface will change and thus the oscillation frequency of the crystal (from $\nu_1$ to $\nu_2$). Such coated piezoelectric crystals are known from gas analysis. The Swedish Pat. No. 434,438 for instance relates to a gas detector, where a gas component of a gas mixture is adsorbed to a thin organic film applied on the surface of a piezoelectric crystal, and the change in oscillation frequency ($\nu_1 - \nu_2$) caused by the increase in mass is a measure of the content of the gas component in question.

It is also known for instance from the U.S. Pat. No. 3,164,004 to coat a piezoelectric crystal with a thin substrate of a solid substance, e.g. silver and copper, and to measure the change in frequency that is caused by chemical or physical interaction between the substrate and a gas stream.

On the other hand, it is not previously known to immerse according to the invention a piezoelectric crystal coated with a substrate into a liquid to determine the content of those components in the liquid that will react with the substrate. When determining the corrosivity of a petroleum product, it is valuable to be able to carry out measurements in the liquid phase, as an evaporation may change the components in the liquid that are to be determined.

When the crystal coated with a metal, e.g. silver, is corroded in a petroleum product, the mass on the crystal surface will increase because of the supply of mainly sulphur to the surface. This gives a decrease in the crystal natural oscillation frequency. Said decrease gives a measure of the mass increase, which in turn is proportional to the amount of corrosive compounds in the petroleum product. As an alternative the corroded layer can be washed away, and the resulting decrease in mass gives an increase in the natural oscillation frequency which is registered.

If the product of the metal and the corrosive substance is easily dissolvable in the surrounding medium, a decrease in mass on the crystal surface can be registered.

The method and the device of the invention can also be used to detect sulphur compounds in other liquids than petroleum products, such as in alcohols and aqueous solutions. Also, the content of sulphur compounds in air, e.g. in sulphur discharges from combustion installations and the like, can be determined after taking up the air in a suitable liquid for analysis according to the invention.

The method and the device of the invention are not limited to measuring the reaction between sulphur compounds and etal. Other compounds can also be analyzed with a suitable choice of material on the crystal. An example thereof is chloride.

The method and the device of the invention can also preferably be used to study interacting and counteracting effects respectively from for instance different sulphur compounds in fuel or an aqueous solution. The invention can here be used as an analytical aid.

As the substrate disposed on the piezoelectric crystal one can use all metals that are attacked by corrosion of the kind in question, e.g. copper, silver, aluminium etc. Non-metallic materials can also be used if the reactivity or corrosivity of the liquid towards these materials is to be determined.

The determination of the natural oscillation frequency of the crystal is carried out after a certain period of incubation in the corrosive liquid. Here the measurement can also be performed in situ, i.e. with the crystal immersed in the liquid. This makes it possible to follow continuously the coure of corrosion if desired.

The contact electrode of a piezoelectric drystal is made of a thin coating of metal, e.g. gold, silver, aluminium etc, that has been evaporated directly onto the crystal surface. In order to be able to use a piezoelectric crystal, which is found on the market already coated with a metal, for corrosion measurements according to the invention, the surface must be reproducible, i.e. the surface must initially be identical at different measuring occasions. In this case the invention also comprises an initial activation step with cleaning in order to pre-treat the crystal to make it reproducible, as well as comprising a crystal detector adapted to the method of the invention.

Before the crystal is cleaned, it must be decapsulated. After this is done, one should avoid storing it in an air atmosphere for a long period of time before the activation is carried out, as the crystal is aged when it is exposed to air for a long period. This should not exceed 3 days. The ageing probably depends thereon, that sulphur compounds, for instance $H_2S$, in the air atmosphere will initiate a corrosion attack on the crystal, which makes it more reactive when it is placed in the corrosion test liquid. This ageing effect has most influence on a subsequent measurement in highly corrosive fuels, while the effect is insignificant when measuring in fuels of low corrosivity.

For a large scale analysis it is impractical to clean the crystal directly before the incubation. Suitably the crystal can be coated with metal at a suitable time before the analysis, e.g. by means of evaporation or cementing thereon, or be decapsulated, if a crystal existing on the market already coated with a metal is to be used, and cleaned and then encapsulated in an inert environment, e.g. in a glass ampoule filled with argon, which is later broken immediately before the incubation in the liquid to be analyzed.

When using a piezoelectric quartz crystal coated with a thin layer of silver, the initial cleaning step consists of for instance an activation of the silver layer by means of etching with a cyanide solution, and in this way the silver surfaces on the crystal are being freed from sulphide and oxide coatings. Silver sulphide and metallic silver react with NaCN and oxygen according to the following:

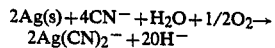

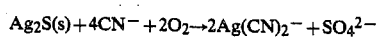

As the metal surface is also attacked, there is probably obtained a breaking up of the surface structure, giving a more reactive surface with shorter analysis times as the result.

In a suitable embodiment of the cyanide activation the silver-coated crystal is etched in 0.01-1M, preferably 0.1M, sodium cyanide solution saturated with oxygen during 10-30 seconds, preferably 10 seconds. If the etching time is too short, problems may arise with the reproducibility of the activation, and if the etching times are too long so much silver may be etched away from the electrode that there is a risk that flakes will scale off or that the silver layer on the crystal is used up.

For the activation also other compounds can be used having similar effects as cyanide, and the choice of compound is made taking into consideration the metal with which the crystal is coated.

Another, very suitable activation process is to pretreat the piezoelectric crystal in a sulphide solution before the corrosivity is measured. The crystal surface will by means of this pretreatment become coated with a very thin sulphide layer, which makes the crystal surface reproducible but also causes the crystal to react earlier, with larger registration and at a lower content of corrosive compounds than if said sulphide coating has not been applied, i.e. the sulphide activation gives the crystal increased sensitivity during the subsequent corrosion measurement. The sulphide layer will then react with sulphur compounds and the like in the corrosive liquid resulting in an increase in the mass on the crystal.

The sulphide activation is suitably carried out in a 0.01-1M, preferably 0.1M sodium sulphide solution for 10-30 seconds, preferably 10 seconds. The concentration of the activation solution is, however, not critical as long as it is above the level where the crystal is saturated with a thin layer of sulphide, which is evident from FIG. 5. An activation time of 10 seconds has proved to be sufficient in most cases, which is evident from FIG. 6.

From FIGS. 5 and 6 there is evident, that the reaction between the sulphide in the aqueous solution during the activation and the crystal occurs very rapidly and is rather an adsorption phenomena. Once a monomolecular layer or thin layer of sulphide on the surface has been adsorbed on the crystal surface, the following reaction occurs very slowly in an aqueous solution. FIGS. 7-9 show that the sulphide-activated crystals react more rapidly with corrosive compounds in a fuel, such as elementary sulphur.

It is also possible to measure by means of the crystal without activating it, but the incubation period must then be prolonged.

If one should wish to use a crysta, which has electrode of a metal that is unsuitable for corrosion measurements, the electrode contact surfaces can be coated with a metal that is more suitable for the corrosion reaction. A gold electrode can for instance be given a silver layer of a suitable thickness by means of thermal evaporation in an evaporation set-up at a low pressure.

After an initial activation, if necessary, of the commercially available, metal-coated piezoelectric crystal or after evaporation of a suitable metal onto a piezoelectric crystal surface, the crystal is placed in the liquid product, whose corrosivity or reactivity is to be determined. The incubation in the test liquid is suitably carried out at a somewhat enhanced, e.g. 50° C., but alower temperature is also possible, for instance in order to lessen the evaporation of the test liquid. The length of the incubation period is to a certain extent adapted to how corrosive or reactive the examined test liquid is. If it is very corrosive, the crystal will soon become overloaded because of the corrosion film, which causes the crystal to stop oscillating. When the test liquid is only weakly corrosive, a longer incubation period of up to 4 hours may be required in order to note a larger frequency change. The incubation period for a silver-coated quartz crystal is usually between 15 minutes and 4 hours and is suitably 1 hour.

Conversion from change in frequency to change in mass can, for gas analysis with coated piezoelectric crystals, be done according to W. H. King Jr., Anal. Chem., 36 (9), 1735 (1964) in accordance with the relationship:

$$\Delta W = \frac{\Delta F \cdot A}{2.3 \cdot 10^6 \cdot F^2}$$

where
$\Delta W$ = change in mass on the electrode surface in gram
$\Delta F$ = change in frequency in Hz
$F$ = natural frequency in MHz
$A$ = electrode area in cm$^2$ This relationship is also applicable for liquid analysis with coated piezoelectric crystals.

BRIEF DESCRIPTION OF THE DRAWINGS

The invention will now be described in more detail in an illustrative but not delimiting purpose by means of a number of examples with reference to the attached drawings, where

FIG. 4 shows the relationship between type and content of mercaptan and the corrosivity in synthetic fuel with 1 mg/l elemetntary sulphur;

DESCRIPTION OF THE PREFERRED EMBODIMENTS

Example 1

Quartz crystals (Kvartselekronik AB, 20 000 MHz 20 ppm hc18/u KVE) with contact surfaces of silver (put on by the manufacturer by means of evaporation) are opened in order to expose the crystal. The crystal and the silver contact surfaces are etched in 0.1 molar sodium cyanide solution for 10 seconds and rinsed in distilled water, 99% ethanol and isooctane. The natural frequency is measured, and then the crystals are incubated for 1 hour at 50° C. in 10 ml jet fuel of different degrees of corrosiveness according to the standard method. Then the crystals are rinsed in isooctane and blown dry. The natural frequency is measured again, and the change for every crystal is registered. The results from the measurements are reported in tables 1 and 2. In the tables there are also reported the corrosiveness according to the standard method and the amount of elementary sulphur determined by means of a polarographic method for every fuel sample.

TABLE 1

Measurements of the corrosivity of jet fuel in some rock chambers installations.

| Installation no. | Corrosion kMz (1 h) | | | | Corrosion Standard IP 227/73 | Elementary sulphur mg/l |
|---|---|---|---|---|---|---|
| 1 | 3.89 | 4.82 | 3.45 | 4.13 | 1 | 0.67 |
| 2 | 9.28 | 10.50 | 11.18 | | 2+ | 1.6 |
| 3 | 4.75 | 5.02 | 4.34 | 4.64 | 2+ | 0.48 |
| 4 | 2.38 | 2.14 | 2.03 | 2.62 | 0+ | 0.14 |

TABLE 2

Measurements of the corrosivity of stored fuel in a rock chamber installation.

| Depth m | Corrosion kHz (1 h) | | | Corrosion Standard IP 227/73 | Elementary sulphur mg/l |
|---|---|---|---|---|---|
| 2 | 0.16 | 0.21 | 0.24 | 0 | 0.2 |
| 4 | 0.25 | 0.25 | 0.19 | 0 | 0.3 |
| 6 | 2.92 | 2.77 | 2.86 | 1 | 0.6 |
| 8 | 4.87 | 4.79 | 4.84 | 2 | 1.0 |
| 10 | 4.99 | 5.61 | 5.89 | 2+ | 1.2 |
| 12 | 6.64 | 6.51 | 5.89 | 2+ | 1.2 |
| Control | 0.35 | 0.33 | | 0 | 0 |

Figure 1:
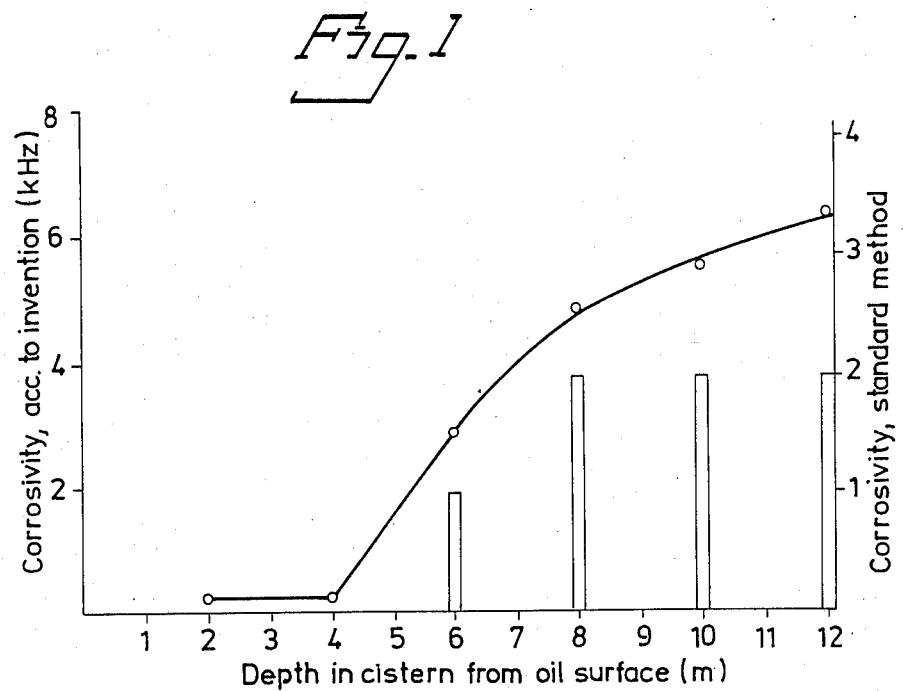
FIG. 1 shows the corrosivity that has been measured at various depths in a cistern when storing jet fuel, according to the method of the invention and according to the standardized test method.

FIG. 1 shows graphically the result in table 2 from sampling at various depths in a cistern, when fuels are stored in rock chambers. From the diagram one can see the increased sensitivity of the method according to the invention compared with the standardized test method, where the result is expressed as an integer from 0 to 4.

Example 2

In order to examine how the change in frequency depends on the corrosivity, a test series has been carried out, where highly corrosive fuel is mixed with different contents of non-corrosive fuel. Crystals are etched and incubated according to example 1.

Figure 2:
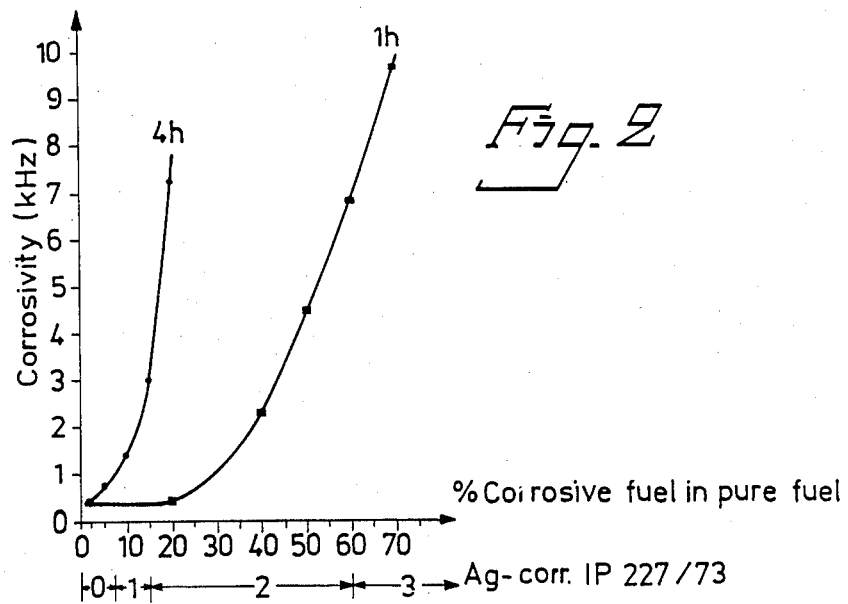
FIG. 2 is a diagram that shows the proportionality between the change in the natural oscillation frequency of the crystal and the content of corrosive compounds in a jet fuel when incubating for 1 hour and 4 hours, as well as the correlation between the method of the invention and the standardized test method.

A mixture of corrosive fuel of classification 3 with fuel of classification 0 (according to the standard method) gives a relationship between the corrosivity and the percentage of the additive as is seen from FIG. 2. It is also valuable to be able to quantitatively estimate how much of a non-corrosive fuel there is required if mixed into a corrosive fuel to make the corrosivity of the mixture acceptable from for instance a flight safety point of view. From the example is also seen the correlation between the crystal method of the invention and the standard method IP 227/73 for this fuel.

Example 3

Figure 3:
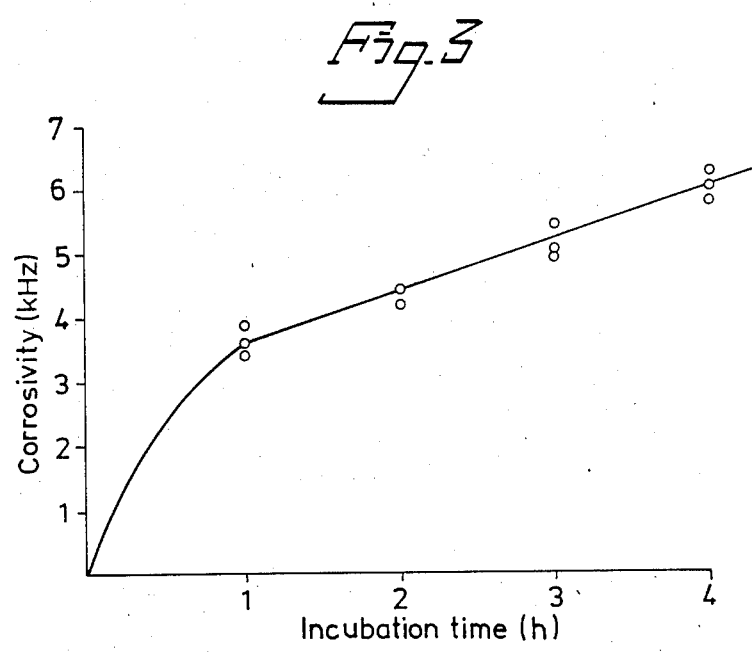
FIG. 3 shows how the frequency change and thus the corrosiveness is changed with the incubation period time.

Crystals according to example 1 are incubated for different lengths of time in a fuel of corrosivity classification 2 according to the standard method, and the measured results are shown in the diagram of FIG. 3. From the appearance of the curve is evident that a linear relationship between the corrosivity and the incubation time is obtained after a certain period of time, here 1 hour.

Example 4

The corrosivity of aviation fuel was determined after incubating crystals according to example 1 for 1 hour and 4 hours. The corrosivity was also determined by means of the standard method IP 227/73 and by measuring the content of elementary sulphur. From FIG. 2 is seen how a longer incubation time can be used in order to be able to detect at an early stage tendencies of corrosivity.

Example 5

Figure 4:
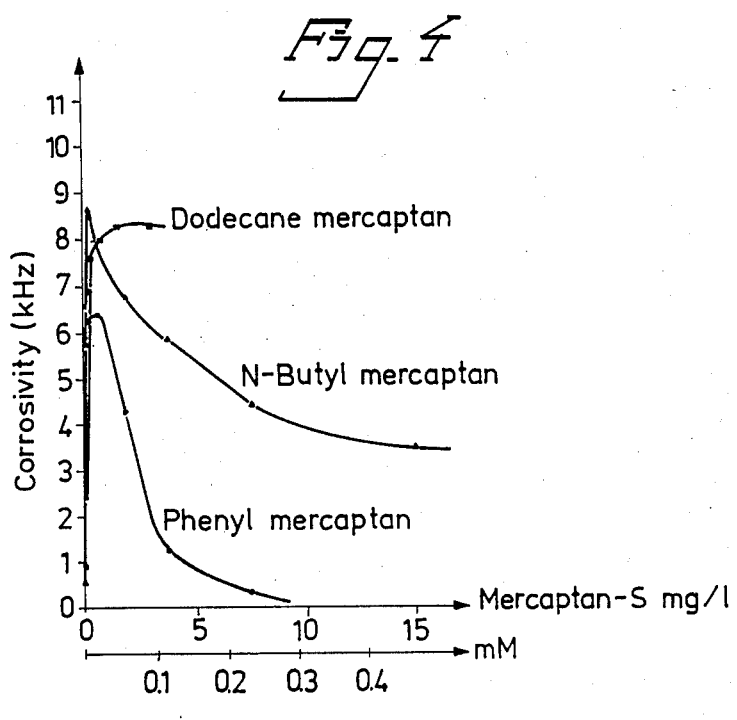
FIG. 4 shows how the method can be used to study the effect by various sulphur compounds, in this case mercaptans, on the corrosivity.
Figure 5:
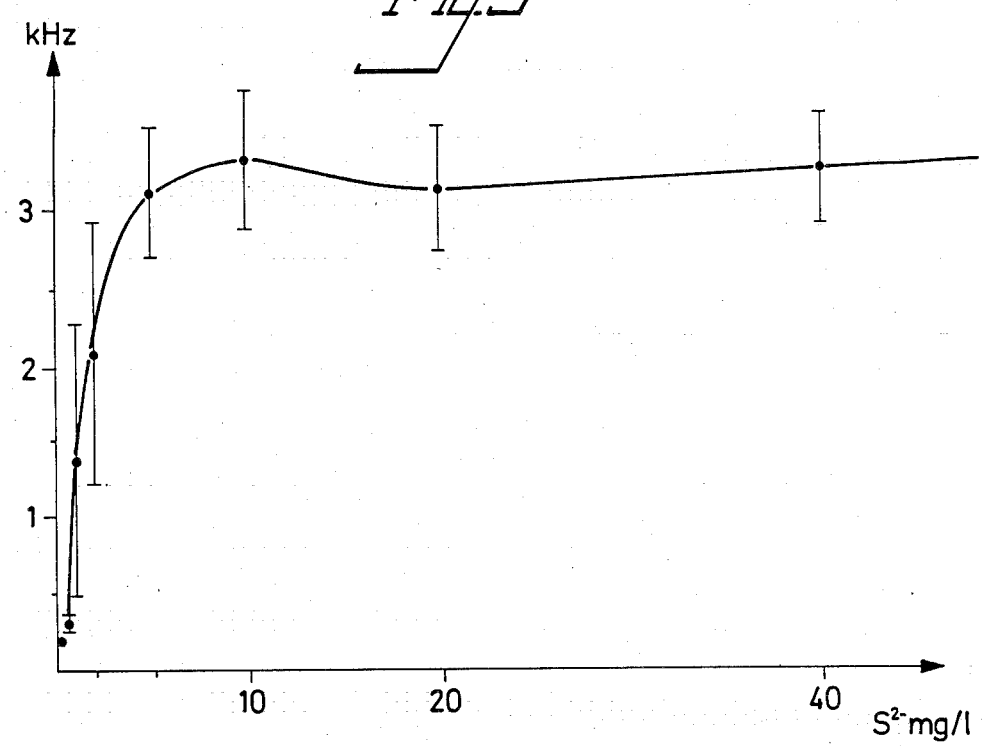
FIG. 5 shows the dependence of the measured corrosivity on the concentration of the activation solutionin the pretreatment step, when activation by sodium sulphide is used. For every measuring point six crystals have been incubated for 4 hours at +50° C. in pure fuel with an addition of 1 mg/l of elementary sulphur.
Figure 6:
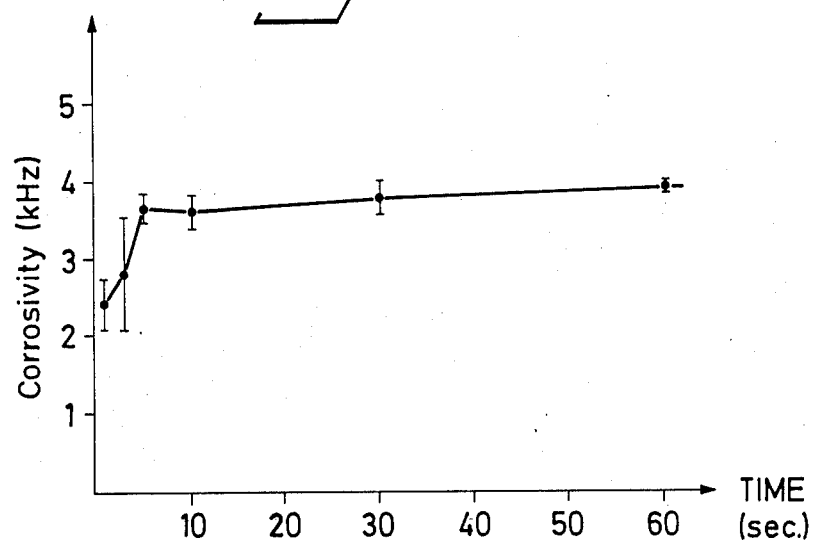
FIG. 6 shows how the length of the activation time in the pretreatment step influences the measured corrosivity, when a 0.001M sodium sulphide solution is used to activate the crystal. For every measuring point six crystals have been incubated for 4 hours at +50° C. in pure fuel with an addition of 1 mg/l of elementary sulphur.

The utility of the method as an analytical aid is seen in FIG. 4, where the corrosivity has been determined after incubating crystals according to example 1 for 1 hour in fuel mixtures with various contents and types of mercaptans.

Example 6

Quartz crystals (Kvartselektronik AB, 20 000 MHz 20 ppm hc18/u KVE) with contact surfaces of silver (put on the manufacturer by means of evaporation) are opened so that the crystal is exposed. The crystal and the silver contact surfaces are heated in one case with 0.1M sodiumcyanide solution and in the other case with 0.1M sodium sulphide solution for 10 seconds and rinsed in distilled water, 99% ethanol and isooctane. The natural frequency is determined, and then the crystals are incubated in 10 ml jet fuel for 1 hour and 4 hours at +50° C. The crystal is then rinsed in isooctane and blown dry. The natural frequency is measured again, and the change is registered for every crystal. In tables 3 and 4 are shown the results of the measurements. In the tables there are also shown the corrosivity according to the standard method and the amount of elementary sulphur determined by means of a polarographic method for every fuel sample.

TABLE 3

Determination of the corrosivity of jet fuel in a rock chamber installation with additions of elementary sulphur utilizing crystals that have been activated by cyanide and by sulphide. The corrosivity had also been determined by means of the standard method IP 227/73 as a reference. Inc = incubation time in the fuel, n = number of crystals, $\bar{x}$ = average value and s = standard deviation

| Amount of added elementary sulphur S mg/l | Corrosion standard IP 227/73 | Corrosivity kHz ||||||||
|---|---|---|---|---|---|---|---|---|---|
| | | Cyanide activation Inc 4 h ||| Sulphide activation Inc 4 h ||| Sulphide activation Inc 1 h |||
| | | n | $\bar{x}$ | s | n | $\bar{x}$ | s | n | $\bar{x}$ | s |
| 0 | 0 | 24 | 0.425 | 0.133 | 6 | 0.637 | 0.083 | — | — | — |
| 0.1 | 0 | — | — | — | 6 | 1.026 | 0.148 | — | — | — |
| 0.3 | 0 | 5 | 0.245 | 0.093 | 6 | 4.236 | 0.308 | — | — | — |
| 1.0 | 0 | 6 | 0.511 | 0.057 | 6 | 12.428 | 0.526 | 6 | 4.90 | 0.215 |

The result shows that by means of sulphide activation, tendencies of corrosivity can be indicated earlier than by means of cyanide activation. No corrosivity can be detected by means of the standard method.

TABLE 4

Measurement of the corrosivity in fuel stored in a rock chamber installation and fuel brought to the installation in a tank car. Determination by means of piezoelectric crystals activated by cyanide solution (0.1 M) and sulphide solution (0.1 M). The corrosivity has also been determined by means of the standard method IP 227/73, and the content of elementary sulphur has been determined polarographically.

| Sample | Depth m | Ag-corr IP 227/73 | Ag kHz 4 h CN$^-$ ||| Ag kHz 4 h HS$^-$ ||| So mg/l |
|---|---|---|---|---|---|---|---|---|---|
| | | | n | $\bar{x}$ | s | n | $\bar{x}$ | s | |
| Cistern | 1 | 0, 0+ | 4 | 0.401 | 0.025 | 2 | 1.880 | 0.019 | <0.2 |
| | 2 | 0, 0+ | 4 | 0.450 | 0.044 | — | | | |
| | 3 | 0+, 0+ | 4 | 0.526 | 0.087 | — | | | |
| | 4 | 0+, 0+ | 4 | 0.565 | 0.023 | | | | <0.2 |
| | 5 | 0+, 0+ | 4 | 0.728 | 0.115 | — | | | |
| | 6 | 1−, 1− | 4 | 0.543 | 0.114 | 2 | 2.346 | 0.111 | <0.2 |
| | 6.75 | 1−, 1− | 4 | 0.560 | 0.227 | 2 | 2.699 | 0.452 | |
| | 7.25 | 1−, 1− | 4 | 0.658 | 0.366 | 2 | 2.552 | 0.129 | <0.2 |
| Average value | | 0+ | | 0.554 | | | 2.37 | | <0.2 |
| Tank car | 1 | 0, 0 | 4 | 0.422 | 0.129 | 2 | 0.692 | 0.252 | <0.2 |
| | 2 | 0, 0 | 4 | 0.482 | 0.142 | 2 | 0.702 | 0.212 | <0.2 |
| | 3 | 0, 0 | 4 | 0.627 | 0.109 | 2 | 0.779 | 0.049 | <0.2 |
| | 4 | 0, 0 | 4 | 0.637 | 0.115 | 2 | 0.470 | 0.011 | <0.2 |
| | 5 | 0, 0 | 4 | 0.646 | 0.109 | 2 | 0.570 | 0.12 | <0.2 |
| Average value | | 0 | | 0.563 | | | 0.643 | | <0.2 |

The result of the measurements shows that by means of the standard method IP 227/73 a faint trace of corrosivity can be noted in the cistern but not in the tank car. By means of the crystal method utilizing cyanide activation, no appreciable difference can be noted, but if one utilizes sulphide activation it is observed that the fuel in the cistern is more corrosive than the fuel brought in the tank car.

Example 7

Figure 7:
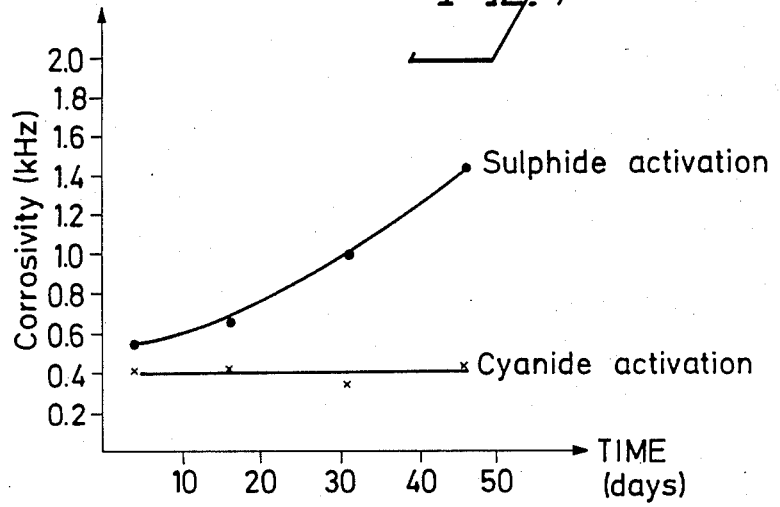
FIG. 7 shows how piezoelectric crystals can be used in order to follow the corrosivity in jet fuel when being stored on a water bed. The corrosivity has been followed for a period of 43 days with crystals activated by sulphide and by cyanide and incubated for 4 hours in the fuel for analysis according to example 6.

In order to examine how piezoelectric crystals can be used to discover early signs of corrosion when jet fuel is stored on a water bed, measurements have been carried out in a model system with water and fuel. In this case a comparison has been done between corrosion determinations by means of sulphide-activated crystals (10 seconds in 0.1M sulphide solution) and cyanide-activated crystals (10 seconds in 0.1M cyanide solution) according to example 6. The incubation time has been 4 hours. The result is seen in FIG. 7.

With sulphide-activated crystals, signs of beginning corrosivity can be discovered early, which is of great importance when jet fuel is stored on a water bed in a rock chamber. In this case signs of corrosion can be discovered already after 30 days.

Example 8

Figure 8:
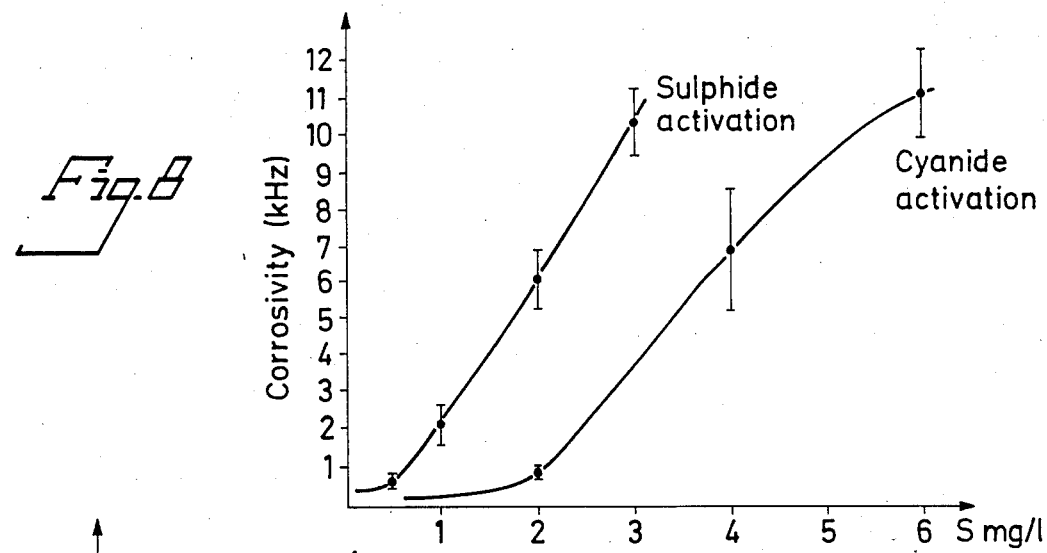
FIG. 8 gives a comparison between crystals activated by sulphide and by cyanide according to example 6, when measuring the corrosivity in fuel, which has been added elementary sulphur in order to increase the corrosivity. Incubation period 1 hour.
Figure 9:
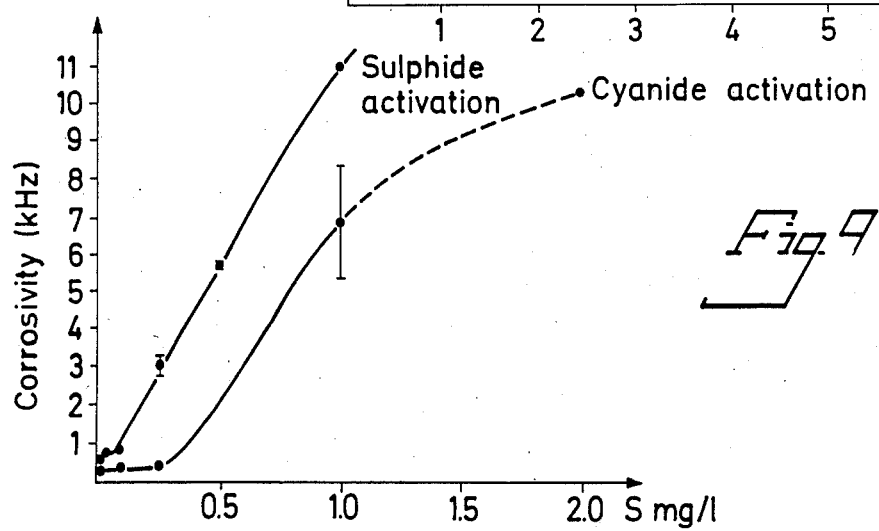
FIG. 9 gives a comparison between crystals activated by sulphide and by cyanide according to example 6, when measuring the corrosivity in fuel, which has been added elementary sulphur in order to increase the corrosivity. Incubation period 4 hours.

In order to examine how the frequency change is dependent upon the corrosivity, two test series were carried out, and measuring by means of cyanide-activated crystals was compared with measuring by means of sulphide-activated crystals. The crystals were treated according to example 6. In one test series an incubation time of 1 hour was used (FIG. 8), and in the other test series an incubation time of 4 hours was used (FIG. 9).

In both test series elementary sulphur was added to non-corrosive fuel in order to give a fuel having an increasing corrosivity.

In both cases it is evident that the sulphide-activated crystals are more sensitivity than the cyanide-activated crystals and can prove corrosivity at an earlier stage. The spreading of the values is also less, when sulphide-activated crystals are used.

Although the invention has been illustrated by means of corrosion determinations in petroleum products, it is submitted that the invention is generally applicable for the analysis of the corrosivity of a liquid.

We claim:

1. Method for measuring the corrosivity of a corrosive liquid comprising the steps of:
   coating a piezoelectric crystal with a layer of a corrodible material;
   cleaning and activating the coating layer of corrodible material by exposing said coating layer to a sulphide solution for a period of time sufficient to provide a thin, reproducible sulphide layer on said coating layer thereby making said coating layer more sensitive to corrosive compounds in the corrosive liquid;
   determining the natural oscillation frequency ($\nu_1$) of the coated and activated piezoelectric crystal;
   exposing the crystal to the corrosive liquid;
   determining the natural oscillation frequency ($\nu_2$) of the crystal after exposure to the corrosive liquid for a certain period of time;
   determining the change in the natural oscillation frequency ($\nu_1-\nu_2$) of the crystal; and
   determining the mass change on the surface of the crystal and thus of the content of corrosive compounds in the liquid from said change in natural oscillation frequency.

2. Method according to claim 1, wherein the piezoelectric crystal is a quartz crystal.

3. Method according to claim 1, wherein the corrodible material is a metal.

4. Method according to claim 1, wherein the step of cleaning and activating the coating layer comprises exposing said coating layer to 0.01–1M sodium sulphide solution for 10–30 seconds.

5. Method according to claim 4, wherein the concentration of the sodium sulphide solution is 0.1M.

6. A corrosivity measuring component comprising:
   a piezoelectric crystal;
   layers of a corrodible material deposited on said piezoelectric crystal; and
   a thin, reproducible sulphide layer provided on said layers of corrodible material;
   wherein, said layers of corrodible material function as electrodes during determination of the oscillation frequency of said piezoelectric crystal; and
   wherein, said thin, reproducible sulphide layer on said layers of corrodible material is formed by pretreating said layers of corrodible material for cleaning and activation thereof by exposing said layers of corrodible material to a sulphide solution.

7. A corrosivity measuring component of claim 6, wherein said piezoelectric crystal is a quartz crystal and said layers of corrodible material comprise silver.

* * * * *